United States Patent [19]
Gulbrandsen et al.

[11] Patent Number: 5,700,790
[45] Date of Patent: *Dec. 23, 1997

[54] PREVENTION AND TREATMENT OF MYOCARDIAL FAILURE

[75] Inventors: Carl E. Gulbrandsen, Madison; Richard L. Moss, Middleton, both of Wis.

[73] Assignee: Bone Care International, Inc., Madison, Wis.

[*] Notice: The term of this patent shall not extend beyond the expiration date of Pat. No. 5,350,745.

[21] Appl. No.: 588,067

[22] Filed: Jan. 17, 1996

Related U.S. Application Data

[63] Continuation of Ser. No. 311,934, Sep. 26, 1994, abandoned, which is a continuation of Ser. No. 10,823, Jan. 29, 1993, Pat. No. 5,350,745.

[51] Int. Cl.$^6$ .................................................. A61K 31/59
[52] U.S. Cl. .................................................. 514/167
[58] Field of Search .................................. 514/167, 168

[56] References Cited

U.S. PATENT DOCUMENTS 4,501,737  2/1985  Yamato et al. .......................... 514/167

OTHER PUBLICATIONS

R.J.S. McGonigle, *Nephron*, vol. 36, No. 2, 1984, pp. 94–100.

A.R.J. Bosley, *Arch. Dis. Child.*, vol. 55, No. 9, 1980, pp. 683–686.

A.M. Feldman, M.D., *Am. J. Kidney Dis.*, vol. 11, No. 1, 1988, pp. 76–79.

G.M. Diffee, *Biophys. J.*, vol. 64, No. 2, Feb. 14, 1993, p. A254, abstract No. W–Pos–30.

M. R. Walters et al., "1,25-Dihydroxyvitamin $D_3$ Receptors Identified in the Rat Hear.," *J. Mol. Cell. Cardiol.*, 1986; 18 pp. 67–72.

R. E. Weishaar and R. U. Simpson, "Vitamin $D_3$ and Cardiovascular Function in Rats," *J. Clin. Invest.*, 1987; 79 pp. 1706–1712.

R. E. Weishaar and R. U. Simpson, "Involvement of Vitamin $D_3$ with Cardiovascular Function II. Direct and Indirect Effects," *Am. J. Physiol.*, 1987; 253 (Endocrinol Metab 16) pp. E675–E683.

J. Sellers and R. Boland, "Rapid Stimulation of Calcium Uptake and Protein Phosphorylation in Isolated Cardiac Muscle by 1,25-dihydroxyvitamin $D_3$," *Mol. and Cell. Endocrinol.*, 1991; 77 pp. 67–73.

Weishaar et al., *Chemical Abstracts*, vol. 112 (15), No. 133090g, 1990.

*Primary Examiner*—William R. A. Jarvis
*Attorney, Agent, or Firm*—Teresa J. Welch; Stroud, Stroud, Willink, Thompson & Howard

[57] ABSTRACT

Method of increasing the strength of contraction in the mammalian heart muscle by administering to the mammal an effective amount of an activated Vitamin D compound, i.e. a 1α-hydroxylated Vitamin D compound which binds with the Vitamin D receptor and produces a positive inotropic effect in the heart muscle. The activated Vitamin D compound may be given as a means to prevent myocardial failure or to treat myocardial failure.

7 Claims, No Drawings

PREVENTION AND TREATMENT OF MYOCARDIAL FAILURE

This application is a continuation of application Ser. No. 08/311,934 filed on Sep. 26, 1994, now abandoned, which is a continuation of application Ser. No. 08/010,823 filed Jan. 29, 1993, now U.S. Pat. No. 5,350,745

FIELD OF THE INVENTION

This application claims priority to PCT/US94/01172 filed Jan. 31, 1994.

This invention relates a method of treating myocardial failure, more specifically it relates to the use of active forms of vitamin D to increase the strength contraction of the heart muscle.

BACKGROUND OF THE INVENTION

Heart failure is a common clinical condition and results in a significant morbidity and mortality. It is defined as the pathophysiologic state in which an abnormality of cardiac function is responsible for the failure of the heart to pump blood at a rate commensurate with the requirements of the metabolizing tissues or can do so only from an abnormally elevated filling pressure. Heart failure is frequently, but not always caused by a defect in myocardial contraction wherein the strength of contraction of the heart muscle is diminished. In such a case, the term myocardial failure is appropriate. Few therapies exist for myocardial failure that are effective and do not present significant undesirable side effects. The most common treatment of myocardial failure is the administration of cardiac glycosides such as digitalis. While digitalis can alleviate the symptoms and improve cardiac hemodynamics in heart failure, it, as well as the other cardiac glycosides, has a low margin of safety. Such potent drugs cause cardiac dysrythmias and neurological problems as well as nausea, abdominal pain and headache. Further, drug interaction problems are reported with the cardiac glycosides and other common drugs.

What is needed is a method of increasing the strength of the heart contraction without the above described undesirable side effects.

DESCRIPTION OF THE INVENTION

The present invention is for a method of treating myocardial failure using an active form of vitamin D. Vitamin D is known to be important in the regulation of calcium metabolism in animals and man. See, *Harrison's Principals of Internal Medicine*: Part Eleven, "Disorders of Bone and Mineral Metabolism", Chapter 335, E. Braunwald, et.al., (eds.), McGraw-Hill, New York, 1987, pp. 1860–1865.

It is known that vitamin $D_3$ must be hydroxylated in the 1 and the 25 position before it is activated i.e. before it will produce a biological response. A similar metabolism appears to be required to activate the other forms of vitamin D e.g. vitamin $D_2$ and vitamin $D_4$. As is generally understood and used herein, the term "vitamin D" is intended to include vitamins $D_3$, $D_2$, and $D_4$. The term activated vitamin D, as used herein, is intended to refer to vitamin D which has been hydroxylated in at least the 1 position of the A ring and binds with the vitamin D receptor. e.g. 1,25-dihydroxyvitamin $D_3$.

The 1α-hydroxyvitamin D of the present invention has the general formula described in formula I wherein A and B are either hydrogen or a carbon to carbon bond thus forming a double bond between C22 and C23, $R_2$, and $R_3$ can be either hydrogen, hydroxy, lower alkyl, O-lower alkyl, O-lower acyl, O-aromatic acyl or flouro, and where $R_4$ is hydrogen or lower alkyl along with an acceptable excipient.

In the formulae shown in this specification and in the claims a wavy line to substituent X indicates that the substituent can be either α or β stereoisomeric form. Wherever in this specification and in the claims the word "lower" is used as a modifier of alkyl or acyl it is intended to identify a hydrocarbon chain having from about 1 to 4 carbon atoms and can be either a straight chain or branched chain configuration.

Specific examples of such hydrocarbon chains are: methyl, ethyl, propyl, butyl, isobutyl or t-butyl, and formyl, acetyl, propionyl,or butyryl. The word "aromatic acyl" as used herein and in the claims is meant to identify a benzoyl group or a substituted benzoyl group such as nitrobenzoyl or dinitrobenzoyl.

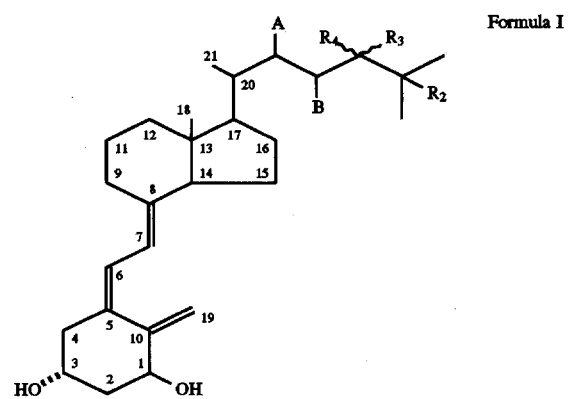

Formula I

Among the preferred active vitamin Formula I D compounds are:

1α,25-dihydroxy-cholecalciferol [1α,25-(OH)$_2$D$_3$]
1α-hydroxy-cholecalciferol[1α-(OH D$_3$]
1α,24-dihydroxy-cholecalciferol[1α,24-(OH)$_2$D$_3$]
1α,25-dihydroxy-ergocalciferol[1α,25-(OH)$_2$D$_2$]
1α-hydroxy-ergocalciferol[1α-(OH)D$_2$]
1α,24(s) -dihydroxy-ergocalciferol[1α,24(s)-(OH)$_2$D$_2$]
1α,25-dihydroxy-vitamin D$_4$[1α,25-(OH)$_2$D$_4$]
1α-hydroxy-vitamin D$_4$[1α-(OH)D$_4$]
1α,24-dihydroxy-vitamin D$_4$[α,24-(OH)$_2$D$_4$]

The above described active forms of vitamin D can be prepared as described in U.S. Pat. Nos. 3,993,675; 4,022, 891; 4,195,027; 4,234,495; 4,508,651 and co-pending U.S. applications 07/940,246 and 07/991,493 all incorporated herein by reference.

Functionally, vitamin D is more appropriately considered a hormone than a vitamin. When activated, vitamin D interacts with a vitamin D receptor protein and this interaction ultimately results in some form of biological response. For example, 1α,25-dihydroxyvitamin D$_3$ is known to be a potent stimulator of calcium absorption from the intestine which is mediated by the interaction of the 1α,25-dihydroxyvitamin D$_3$molecule and the vitamin D receptor protein located in the epithelial cells (enterocytes) which line the intestine.

In recent years it has become evident that the vitamin D receptor protein is widely distributed in the bodies of animals and man. Thus, it is not surprising that besides calcium homeostasis, activated vitamin D has been implicated in osteogenesis, modulation of immune response, modulation of the process of insulin secretion by the pancreatic B cell, muscle cell function and the differentiation and growth of epidermal and hemopoietic tissues.

More recently, 1α,25-dihydroxyvitamin D$_3$ receptors have been shown to exist in the rat heart,(Walters et. al., J.

Mol. Cell Cardiol. 18:67–72 (1986)) and this has prompted the speculation that vitamin D may play a role in cardiac function. Until the present invention, the prevailing view, which was based on studies of cardiac hemodynamics in vitamin $D_3$ deficient rats, was that $1\alpha,25$-dihydroxyvitamin $D_3$ produced a direct negative inotropic effect in the heart, presumably by promoting the sequestering of calcium in the myocardium. (Weishaar and Simpson, Am. J. Physiol. 253 (Endocrinol. Metab. 16): E675–E683 (1987).

Contrary to the hypothesis of Weisharr and Simpson, the present inventors have found that active forms of vitamin D, including $1\alpha,25$-dihydroxyvitamin produce a direct positive inotropic effect in the mammalian myocardium i.e. increases the strength of the contraction of the heart muscle.

Example 1: Positive inotropic effect

Rat right ventricular papillary muscles were mounted in an experimental chamber and stimulated at 0.3–0.7 Hz with a single pulse, broad field stimulation via platinum plate electrodes. The preparation was continuously perfused at 22°–24° with oxygenated modified Tyrode's solution, pH 7, containing 2 mM $Ca^{2+}$. Twitch tension of the preparation was measures by suturing one end of the preparation to a force transducer and the other end to a three way positioner. Muscles attaining a stable baseline twitch tension were then perfused with 0.1 to 6.25 µM of $1\alpha,25$-dihydroxyvitamin $D_3$. In nine experiments $1\alpha,25$-dihydroxyvitamin $D_3$ increased steady-state twitch tension an average $14\pm11\%$ (range of 4–41%). The effects of $1\alpha,25$-dihydroxyvitamin $D_3$ were reversed by drug washout. These results indicate that $1\alpha,25$-dihydroxyvitamin $D_3$ has a positive inotropic effect on the mammalian myocardium.

Example 2: prevention of Congestive Heart Failure

An oral dosage formulation containing $1\alpha,25$-dihydroxyvitamin $D_3$ is evaluated in a double blind study for efficacy in the preventing the development of heart failure caused by myocardial failure. The formulation evaluated contains 0.25 µg of $1\alpha,25$-dihydroxyvitamin $D_3$. The control formulation is identical except that it does not contain the $1\alpha,25$-dihydroxyvitamin $D_3$. Five hundred normal subjects between the ages of 55 and 65 are selected. The subjects are divided into an experimental and control population. They are instructed to take the medication twice a day, in the morning and in the evening.

Evaluations of cardiovascular hemodynamics, are conducted at six month intervals by a physician. The final evaluation is carried out at the end of three years of preventive therapy. The results of the study show that daily oral administration of 1,25-dihydroxyvitamin $D_3$ significantly reduces the occurrence of myocardial failure in the experimental group as compared with the control.

As the above example illustrates, preventive benefit in reducing the occurrence of myocardial failure is derived from daily administration of a relatively low dosage of $1\alpha,25$-dihydroxyvitamin $D_3$. For treatment purposes, however, a higher dosage would be desired. However, the vitamin $D_3$ compounds, particularly, $1\alpha,25$-dihydroxyvitamin $D_3$ cannot safely be administered at a dosage greater than 1.0 µg per day without causing hypercalcemia and hypercalciuria in a large portion of the population. In that regard the active forms of vitamin $D_2$ and vitamin $D_4$ are more suitable for while they display a high binding activity with respect to the vitamin D receptor they have a much lower calcemic effect and are thus much less toxic. See for example co-pending U.S. application Ser. No. 07/940,246 which is incorporated herein by reference. Preferred in this regard are $1\alpha$-hydroxy-ergocalciferol[$1\alpha$-(OH)$D_2$], $1\alpha,24(s)$-dihydroxy-ergocalciferol[$1\alpha,24(s)$-(OH)$_2D_2$], $1\alpha$-hydroxy-vitamin $D_4$[$1\alpha$-(OH)$D_4$] and $1\alpha,24$-dihydroxy-vitamin $D_4$[$1\alpha,24$-(OH)$_2D_4$].

Advantageously, the vitamin $D_2$ and $D_4$ compounds of the present invention or combinations thereof with other therapeutic agents can be administered in dosage amounts of from 0.1 to 10.0 micrograms per day. These compounds can be administered as sterile parenteral solutions by injection or intravenously or by alimentary canal in the form of oral dosages, or by suppository. In relation to treatment of early stage myocardial failure doses from about 1.5 to about 6.0 micrograms per day are generally effective. For more advanced stages of myocardial failure, it may be advisable to administer the compounds of the present invention in conjunction with more traditional therapies such as the cardiac glycosides. Surprisingly it is found that the compounds of the present invention produce a synergistic response when administered in conjunction with another positive inotropic compound such as the glycosides. This synergistic effect allows the physician to administer a lower dosage of the glycosides and helps to avoid many of the undesirable side effects of the glycosides. If the compounds of the present invention are administered in combination with other therapeutic agents, the proportions of each of the compounds in the combination being administered will be dependent on the particular agents being used and the degree of heart failure being treated. It being understood that the specific dosage administered in any given case will be adjusted in accordance with the specific compounds being administered, the stage of the myocardial failure to be treated, the condition of the subject and the other relevant medical facts that may modify the activity of the drug or the response of the subject, as is well known by those skilled in the art.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method for preventing myocardial failure in a mammal in need thereof comprising administering to said mammal an effective amount of a compound of the general structure of Formula I

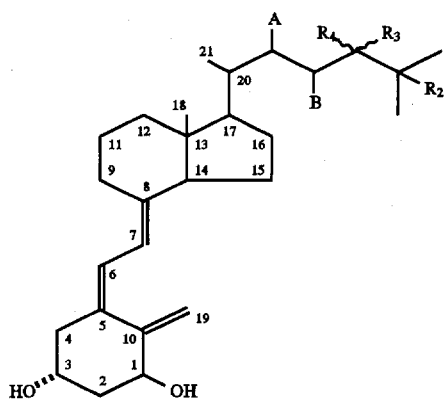

Formula I

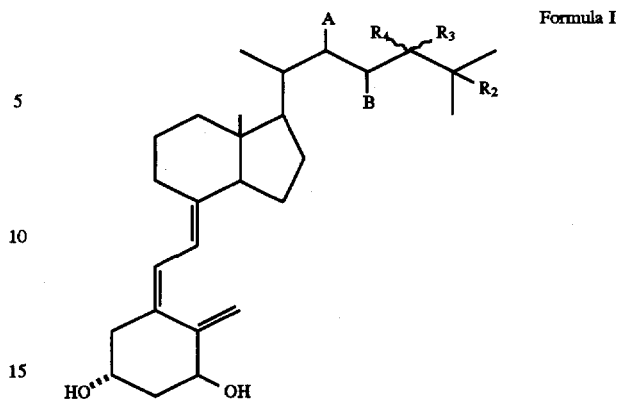

Formula I wherein A and B are either hydrogen or a carbon to carbon bond thus forming a double bond between C22 and C23, $R_2$ and $R_3$ can be either hydrogen, hydroxy, lower alkyl, O-lower alkyl, O-lower acyl, O-aromatic acyl or flouro, and where $R_4$ is hydrogen or lower alkyl along with an acceptable excipient.

2. A method for preventing myocardial failure as described in claim 1 wherein the compound of Formula I is selected from the group consisting of 1α,25-dihydroxycholecalciferol, 1α-hydroxy-cholecalciferol, 1α,24-dihydroxy-cholecalciferol, 1α,25-dihydroxy-ergocalciferol, 1α-hydroxy-ergocalciferol, 1α,24(s)-dihydroxy-ergocalciferol, 1α,25-dihydroxy-vitamin $D_4$, 1α-hydroxy-vitamin $D_4$, 1α,24-dihydroxy-vitamin $D_4$.

3. A method for reducing the occurrence of myocardial failure in a mammal in need thereof comprising administering to the mammal an effective amount of a compound of general Formula I wherein A and B are either hydrogen or a carbon-to-carbon bond, thus forming a double bond between C-22 and C-23, $R_2$ and $R_3$ are either hydrogen, hydroxy, lower alkyl, O-lower alkyl, O-lower acyl, O-aromatic acyl or fluoro, and $R_4$ is hydrogen or lower alkyl along with an acceptable excipient.

4. The method of claim 3 wherein said amount is 0.25 µg administered twice daily.

5. The method of claim 3, wherein A and B are hydrogen and $R_4$ is methyl or A and B form a double bond and $R_4$ is methyl.

6. The method of claim 5 wherein said amount is from 0.1 µg to 10.0 µg per day.

7. The method of claim 3 wherein said compound is administered in combination with a cardiac glycoside.

* * * * *